United States Patent [19]

Norman et al.

[11] Patent Number: 5,038,046

[45] Date of Patent: Aug. 6, 1991

[54] METHOD AND GENERATOR FOR PRODUCING RADIOACTIVE LEAD-212

[75] Inventors: John H. Norman; Wolfgang A. Wrasidlo, both of La Jolla; Karol J. Mysels, San Diego, all of Calif.

[73] Assignee: Biotechnetics, A Brunswick Corporation, San Diego, Calif.

[21] Appl. No.: 550,468

[22] Filed: Jul. 10, 1990

[51] Int. Cl.$^5$ .............................................. G21G 4/06
[52] U.S. Cl. ................................ 250/432 PD; 423/2; 423/89; 252/645
[58] Field of Search .............. 250/432 PD; 423/2, 89; 252/645, 644

[56] References Cited

U.S. PATENT DOCUMENTS 3,801,818  4/1974  Hulit et al. .................. 250/432 PD
4,663,129  5/1987  Atcher et al. ................ 250/432 PD

OTHER PUBLICATIONS

Zucchini et al., Int. J. Nucl. Med. Biol., vol. 9, No. 1, 1982, pp. 83–84.

Primary Examiner—Jack I. Berman
Attorney, Agent, or Firm—Pretty, Schroeder, Brueggemann & Clark

[57] ABSTRACT

A method and generator for preparing the radioisotope of lead, $^{212}Pb$, whereby $^{228}Th$, in a closed chamber, is allowed to decay to gaseous $^{220}Rn$ which is then readily separated from the thorium and other decay products by diffusing the $^{220}Rn$ gas into a second chamber, where it decays to $^{212}Pb$ which can then be collected from the second chamber. The $^{228}Th$ preferably is amorphous, such as thorium stearate. Collection of $^{212}Pb$ occurs in a medium of high and open porosity into which the $^{220}Rn$ diffuses so that the decay products recoil into the medium. The $^{212}Pb$ can be recovered from this medium by dissolving the medium or by reacting it with an antibody-chelating complex solution to entrap it in the antibody-chelating complex.

24 Claims, 1 Drawing Sheet

METHOD AND GENERATOR FOR PRODUCING RADIOACTIVE LEAD-212

This invention relates generally to the production and isolation of radioisotopes and more particularly to a method and generator for producing lead 212 ($^{212}$Pb) from thorium-228 ($^{228}$Th).

BACKGROUND OF THE INVENTION

Radioactive isotopes have a variety of applications. The choice of an appropriate isotope for any particular use depends on such factors as its half life and the type and energy of the radiation produced. The usefulness of certain isotopes may, however, be severly curtailed by the difficulty of their production and isolation.

Radiation therapy has long been used in the treatment of cancer and other localized lesions. The development of monoclonal antibodies, which can be targeted to specific cells with a high degree of specificity, has made it possible to selectively deliver radioactive agents predominantly to specifically targeted cells. The choice of an appropriate radioactive isotope is the critical aspect in targeting radiation therapy. An appropriate radioactive isotope should, desirably, have a half life which is long enough to permit any necessary logistic and pharmaceutical operations (transport, reaction, sterilization, etc.) prior to administration and arrival at the targeted cell after administration, without much loss of activity and damage in route, but is short enough so that therapeutic action proceeds rapidly. Generally one also desires radiation which is highly cytotoxic at short range so that the cell to which the antibody is attached is killed (as well as immediately adjacent cells that are likely to be also pathogenic) but harmless over longer distances so as not to injure healthy surrounding tissue. Absence of harmful persistent residues is also important.

Many potential radioactive candidates require a cyclotron for production and cannot be seriously considered for regular therapeutic use because of cost and availability reason. Of those possible candidates that do not need to be produced in a cyclotron, $^{212}$Bi and $^{212}$Pb have received considerable attention because they have acceptable decay form, energy, and half life characteristics.

While methods for producing both $^{212}$Bi and $^{212}$Pb are known, most require the use of complex equipment having a rather short life span. One less complicated, long lived generator for producing both $^{212}$Bi and $^{212}$Pb is shown in the literature by Zucchini et al., Intl. J. Nucl. Med. & Bio., Vol. 9, pp. 83 to 84 (June 1982). To produce $^{212}$Pb in this generator, a bed of sodium titanate is maintained in a quartz column in which $^{228}$Th in the tetravalent state and radium-224 ($^{224}$Ra) can be adsorbed above a coarse fritted glass disk sealed in the column. When water is passed through the titanate, $^{220}$Rn, which is a decay product of $^{224}$Ra, dissolves in the water. The water containing the $^{220}$Rn passes through the fritted disk and is collected in a glass reservoir containing 2 cc of water therebelow. Since substantially all of the $^{220}$Rn decays within 5 minutes in the water to $^{212}$Pb, this provides sufficient delay. The water containing the $^{220}$Rn is passed from the reservoir into a column containing a strongly acidic ion exchange resin, such as Bio-Rad AG-50 WX18 cation exchange resin (Bio-Rad, Richmond, Calif.), which adsorbs $^{212}$Pb as the water passes through the column. After sufficient $^{212}$Pb has been absorbed, the resin column is removed and the $^{212}$Pb eluted therefrom using 2N HCl to convert the lead isotope to PbCl$_3$. However, residual radioactivity and contamination was reported when this procedure was used, apparently due to a small amount of $^{228}$Th and $^{224}$Ra eluted. To reduce the contamination an additional ion exchange treatment is required.

There thus exists a need to provide an apparatus and method by which certain useful radioactive isotopes can be efficiently and safely produced. The present invention satisfies this need and provides related advantages as well.

SUMMARY OF THE INVENTION

The present invention provides a method and apparatus for producing radioisotopes which are formed as decay products from rare gases, which are in turn decay products of an element which can be immobilized.

The invention provides a method of obtaining daughter isotopes produced from the decay of a parent isotope via a rare gas intermediary by providing the parent isotope in gaseous contact with a gas permeable barrier impervious to the parent isotope, permitting gaseous intermediary isotopes to diffuse through the gas permeable barrier into a receiving chamber containing an open porosity porous medium, maintaining the gaseous intermediary the open porosity porous medium for a time sufficient to permit at least a portion of the rare gas intermediaries to decay into the daughter isotopes which recoil into and are captured by the open porosity porous medium and recovering from the open porosity porous medium a material whose principal radioactivity is that of the daughter isotopes. A generator for performing the process is also provided.

In one embodiment, the parent isotope is $^{228}$Th from which the daughter is $^{212}$Pb. The open porosity medium can be, for example, urea, glucose, inorganic salts, lyophilized antibody or microspheres.

DETAILED DESCRIPTION OF THE PREFERRED EMBODIMENT

Figure 1:
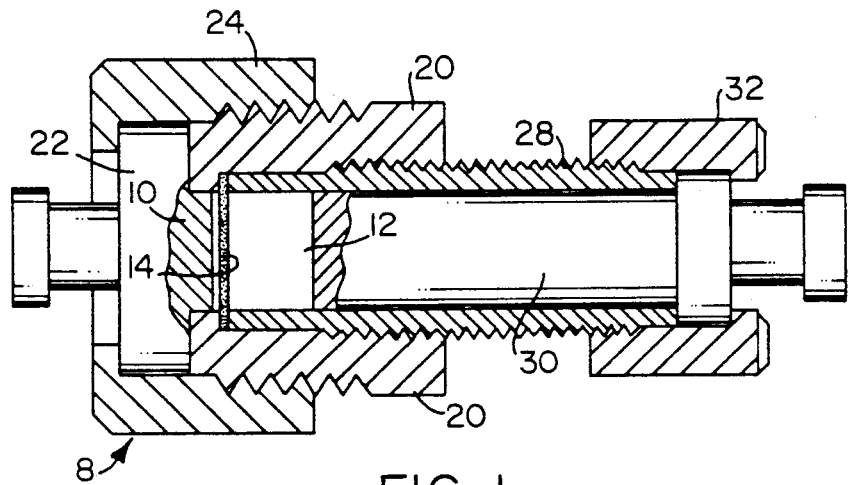
FIG. 1 is a sectional view of a diffusion generator as may be utilized in the practice of the process of the present invention.

This invention is directed to a simple and inexpensive process and a generator for producing radioactive isotopes which is rapid, simple and substantially free of contamination. An important advantage of the generator of this invention is that the parent isotope, which may be highly radioactive and difficult to handle and long lived, is contained in a parental chamber from which only the short lived radon isotope can readily escape. On the other hand, the receiving chamber can be readily loaded with the open porosity porous medium and the latter readily recovered therefrom when desired. Thus the generator can be loaded with the parent isotope in a facility adapted to handle high radiation levels and then transported and used for a long time at a hospital or radio-pharmacy where only the open porosity medium needs to be handled.

In one embodiment, the process and generator of the present invention involve the decay of a parent isotope, such as $^{228}$Th, within a first closed chamber to yield a gaseous decay product, such as $^{220}$Rn, and then allowing the gaseous decay product to diffuse to a second closed receiving chamber, thereby effectively separating the gaseous decay product from the parent and from other solid decay products. The second closed chamber contains an open porosity porous medium, which can be water soluble, such as a bed of powdered urea or sucrose, into the open porosity of which the radon can diffuse. Decay of $^{220}$Rn to $^{212}$Pb (via very short lived polonium-216) causes recoils which tend to embed the lead in the open porosity porous medium as well as in any other solid exposed to the radon. Because of the rapid diffusion of the radon and the large fraction of the gas phase of the generator being within the pores of the open porosity porous medium a majority of the $^{212}$Pb is deposited on and within this medium. Of course, the $^{212}$Pb thus deposited undergoes normal radioactive decay so that the amount thus made available in the open porosity porous medium first increases rapidly but then tends to an equilibrium value, after operation for several half lifes of $^{212}$pb.

It should be noted that the amount of $^{212}$Pb (and of the other isotopes involved) are extremely minute. Thus 1 mCi of $^{212}$Pb corresponds to approximately $2 \times 10^{12}$ atoms of this element which is $3.3 \times 10^{12}$ moles. Hence the handling and reacting of this lead requires special precautions and procedures which are, however, known in the art. Thus the open porosity porous medium can be dissolved in the presence of mild complexing agents and of traces of "cold" (i.e. non-radioactive) lead, prior to the conjugation reaction with the desired antibody. It may then be removed by dialysis or ultrafiltration and the retentate sterilized and used. On the other hand, if the open porosity porous medium is formed by lyophilized fine latex solids, these may be redispersed in water, conjugated with the antibody and injected, with the $^{212}$Pb embedded in them.

As used in the practice of the present invention, the $^{228}$Th is in a physical form that does not create a major barrier to the diffusion of the $^{220}$Rn gas formed as the $^{228}$Th decays, and preferably is amorphous or microcrystalline. As the quantity of $^{228}$Th required is extremely small, it will normally be diluted with a carrier for ease of handling and to dilute radiation damage produced by its decay. Alkaline-earth compounds, particularly barium salts are a preferred diluent because of their chemical similarity to thorium. Among such salts, those of the higher aliphatic acids, particularly stearate and palmitate are preferred as these are known to readily release the radon as it is produced (they have high "emanating power") as described by A. C. Wahl and W. R. Daniels, J. Inorg. Nucl. 6:278–287 (1958), which is incorporated herein by reference.

Alternatively, $^{228}$Th compounds can be ground into super fine particles which are dispersed in a matrix selected from the group consisting of similarly powdered graphite, alumina, and inert ceramic.

As used herein, the term "gas permeable barrier" refers to a chemical or physical barrier which would serve to constrain the immobilized parent isotope but which is permeable to the gas phase intermediary. Examples of such barriers include layers of open-porosity solids such as stainless steel (or other metal) screens or sintered powder, ceramic porous discs, porous plastics, microporous membranes.

As used herein, "recovering" as it refers to the desired daughter isotopes means obtaining the daughter isotopes either with or from the open porosity porous medium. For example, where the open porosity porous medium is water soluble, the open porosity porous medium can be dissolved in water in order to obtain a solution whose principal radioactivity results from the daughter isotopes. Alternatively, where the open porosity porous medium is lyophilized microspheres or antibody, the material can be removed and utilized directly. Thus while in some cases the isotopes are extracted or otherwise removed from the open porosity porous medium, it is also intended that the porous medium, it is also intended that the medium itself, or a derivative, can be used without separating the isotopes therefrom.

As used herein, the term "open porosity porous medium" refers to a solid of substantial bulkiness so that when placed in the receiving compartment the pores within this solid form an important part of the gas phase within the generator and especially of that within the receiving chamber. This porosity is "open" in the sense that it is interconnected so that the gaseous intermediaries can readily diffuse into it, preferably into most of it. Many powders when simply poured into the receiving chamber satisfy these requirements, as do many lyophilized materials. The solid itself has sufficient density such that substantially all of the recoiling daughter will be captured by the open porosity porous medium prior to reaching the side of the container defining the closed chamber. Examples of such open porosity porous media include powdered urea, glucose or other sugars, or inorganic salts; lyophilized antibodies or microspheres. In addition, the open porosity medium must satisfy chemical and biological requirements depending on the use of the daughter isotope, such as being soluble or dispersible in water, being separable from the antibody conjugate, being free of objectionable impurities, particularly other heavy metals, and the like. Such requirements will vary with the particular utilization desired.

Among solids which form suitable open porosity porous media are urea, particularly the ultra-pure grade obtainable from ICN Biochemicals, of Irvine, California, glucose, and sodium chloride, as well as lyophilized materials such as proteins, antibodies, latexes and other particles.

Microspheres as used in this invention are spheres of less than 10 $\mu$m in diameter and more than about 0.02 $\mu$m, generally made from polymers such as polystyrene, polymethyl-methacrylate, available commercially as aqueous dispersions. Lyophilization is a process by which solvent, such as water, is removed from a frozen solution or dispersion by sublimation of the solvent. In order to facilitate the redispersal of the solute, a wetting agent such as Triton 100 can be added.

Although the invention can be used to generate various isotopes as long as they decay through a gas phase intermediary, the invention will be described with particular reference to producing $^{212}$Pb from $^{228}$Th. Generating $^{212}$Pb from $^{228}$Th as taught by the present invention provides a quick, on-site generation and isolation of a high purity product. The process and generator of the present invention produces $^{212}$Pb simply, efficiently, and economically in a most desirable form that can be used in any desired application.

The complete sequence of the spontaneous radioactive decay of $^{228}$Th is shown in Table I. For the purpose of this invention this can be simplified to the following scheme

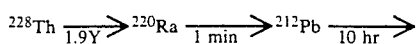

$$^{212}\text{Bi} \xrightarrow{1 \text{ hr}} {}^{208}\text{Pb stable}$$

indicating the main isotopes and their approximate half lives. During each indicated decay alpha, gamma, and in some cases, beta radiations are produced (except in the decay of $^{212}$Pb which produces only betas and gammas).

The therapeutic potential of $^{212}$Pb (or its daughter $^{212}$Bi) is due mainly to its providing alpha particles of about 6 and 9 MV energy which correspond to some 40 and 90 $\mu$m penetration in tissue i.e., killing some 4 to 8 cells. This characteristic permits reaching not only the cancer cells corresponding to the antibody used but also other cells which do not respond but are in close vicinity. On the other hand, healthy cells, not in the immediate vicinity of the target ones, are not affected by these alpha particles. While the 10.6 hour half life of $^{212}$Pb before decaying is perhaps on the short side of ideal for uses such as cancer therapy, it is a very acceptable length of time to allow for production and purification of the therapeutic complex, administration of the complex to the patient, and time of exposure to the cancer cells.

Thorium-228 has a half life of almost two years and is available commercially which makes it highly desirable as a parent isotope. The raw material for charging the parental chamber of the generator of this invention is thus readily obtained and once charged, the generator could be used for a year or more with only gradual loss of productivity.

Radon-220 being a rare gas will, if allowed, rapidly diffuse away from the thorium and other solids of the parental chamber. With a half-life of only about a minute, it decays to give the desired $^{212}$Pb. In order to utilize the radon efficiently it is desirable that as much of its decay as practicable occur within the open porosity porous medium. This is facilitated in two ways according to the preferred embodiment of this invention.

1) The thorium is in a matrix having high emanating power. The distance between the parent source and the receiving open porosity medium is made short. The porous membrane separating the two chambers has a large area, high porosity and slight thickness.

2) The volume of the parental chamber is made as small as practicable compared to that of the pores of the open porosity porous medium. A stable gas will distribute itself proportionately to the available gas-phase volumes. As radon is being generated and is decaying, its concentration is decreasing from the source to the distal end of the open porosity medium, and diffusion continuously proceeds in this direction. Experiments showed that little is gained by making the receiving chamber much longer than about 1 cm as most of the radon would decay before diffusing much longer distances. By using a shorter column of the open porosity medium one can obtain a smaller amount but a higher concentration of the daughter isotope and vice versa.

TABLE I

| Isotope | Half Life | Radiation | Energy (Mev) |
|---|---|---|---|
| $^{228}$Th | 1.9 Years | Alpha | 8.41 |
| $^{224}$Ra | 3.6 Days | Alpha | 5.68 |
| $^{220}$Rn | 54.5 Seconds | Alpha | 6.28 |
| $^{216}$Po | 0.15 Second | Alpha | 6.77 |
| $^{212}$Pb | 10.6 Hours | Beta | 0.35 |
| $^{212}$Bi | 60.5 Minutes | Beta | 2.24 |

TABLE I-continued

| Isotope | Half Life | Radiation | Energy (Mev) |
|---|---|---|---|
| | | Alpha | 6.05 |
| $^{212}$Po | $3 \times 10^{-7}$ Sec. | Alpha | 8.78 |
| $^{208}$Tl | 3.1 Minutes | Beta | 1.42 |
| $^{208}$Pb | (Stable) | | |

Figure 2:
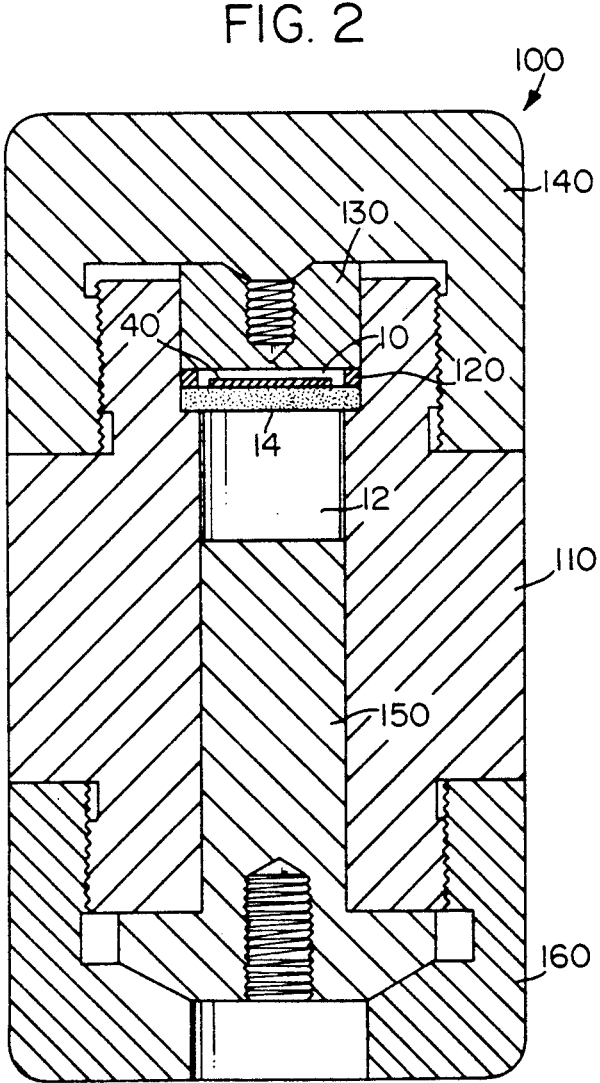
FIG. 2 is a sectional view of an alternate embodiment of the generator as can be utilized in a preferred practice of the process of the present invention.

A generator which can be utilized in the practice of this invention is illustrated in the Figures. The generator can be remotely manipulated in a closed shielded chamber or can be handled in a glove box. As shown in FIGS. 1 and 2, the generator comprises a parental chamber 10, a receiving chamber 12, and a gas elute means such as gas permeable membrane 14 interposed between and separating the two chambers 10 and 12. The gas permeable membrane 14 must have a pore size sufficient to permit the rapid diffusion of the gaseous intermediary therethrough while, at the same time, preventing the parent isotope from passing into receiving chamber 12. For safety purposes, diffusion membrane 14 preferably comprises a porous support member such as a fritted metal disk which can be made from stainless steel. The generator shown in FIG. 1 is formed by a threaded tubular housing 20 having one end thereof closed by end cap 22, which is held in place by flanged cap nut 24. The interior portion of tubular housing 20 has an internal flange 26 at one end thereof which encircles the interior cylindrical surface, and against which the diffusion membrane 14 is positioned. Diffusion membrane 14 should be spaced from end cap 22 by a small distance sufficient to form parental chamber 10 between end cap 22 and the diffusion membrane 14. Parental chamber 10 should be small compared to receiving chamber 12 as indicated above. The volume of receiving chamber should be at least 5 times and preferably 20 times larger than the volume of the parental chamber.

Bushing 28 is threaded into the other end of tubular housing 20 such that its circular inner edge holds diffusion membrane 14 against flange 26, thereby defining one end of a smooth interior cylindrical chamber. An elongated end cap 30 is slidably inserted into the cylindrical chamber within bushing 28 so as to form collection chamber 12 between diffusion member 14 and the inner end of end cap 30. Flanged nut cap 32 is threaded onto bushing 28 to hold end cap 30 in place. For safety reasons, all of the structural components of generator 8 are preferably fabricated of a material that will not absorb the $^{220}$Rn gas or be decomposed by radiation, and has a melting point in excess of 1,000° C. for fire safety. A particularly preferred material is 316 stainless steel.

In accordance with the preferred practice of this invention, the starting material, i.e., $^{228}$Th, is used in a physical form that does not create a barrier to the diffusion of the $^{220}$Rn gas formed as the $^{228}$Th decays. For example, $^{228}$Th can be obtained commercially in the form of thorium-228 nitrate (from Isotope Products Laboratories in Burbank, Calif.). Wahl and Daniels, Supra, teach the coprecipitation of $^{228}$Th and barium stearates. Their procedure involves heating aqueous solutions of sodium stearate to "60-75" degrees centigrade. This causes problems with vapor condensation in a usual, unventilated, glove box. Any ventilation must insure the decay of $^{228}$Rn which is continuously produced and is not adsorbed by conventional filters. Therefore, according to this invention, spiked barium stearate is produced by a metathetical reaction in solution between barium nitrate and a stearate which is soluble at room temperature such as tetramethyl ammonium stearate. The latter is in turn produced by reaction of tetramethyl ammonium hydroxide with stearic acid. Tetra ethyl ammonium hydroxide or the tetra butyl or tetra isopropyl compounds may also be used.

The tetramethyl ammonium stearate solution is prepared outside the glove box by heating an excess of stearic acid with a tetraethyl ammonium hydroxide solution and adding the latter until phenolphthalein indicator turns pink. In the glove box, the $^{228}$Th solution is added to a barium nitrate solution and the excess nitric acid (accompanying the thorium) is neutralized with tetraethyl ammonium hydroxide. Then, with good stirring, the stearate solution is added gradually to the barium spiked solution. The precipitate flocculates near the equivalence point and near neutrality. It is then filtered, sucked dry and placed with the filter in the parental chamber of the generator and dried over silica gel. The parental chamber is then closed.

If the receiving chamber is also closed, i.e., both plungers 22 and 30 are inserted and secured with end caps 24 and 32, the escape of radon from the generator is prevented and it can be removed from the glove box and stored in any appropriately shielded space or transported to another laboratory or hospital.

The generator is ready to produce the daughter isotopes whenever the receiving chamber is loaded with the open porosity medium and closed. This can be done in a chemical hood or a more sophisticated containment as the amount of radon escaping in the short time required, is minimal. Once closed, the generator can be stored in s shielded place. After a time necessary for the desired amount of $^{212}$Pb to accumulate, the reactor is taken back into the hood, the receiving compartment opened and the open porosity porous medium removed and a material containing the daughter isotope recovered, such as by pouring the open porosity porous medium into an aqueous solution of a mild complexing agent for lead. The receiving chamber is then reloaded if desired and closed. After a short time, sufficient for the radon released upon opening the receiving chamber (and that contained in the open porosity medium) to decay adequately, the solution can be removed from the hood and used for the preparation and administration of a therapeutic product.

Alternatively, the $^{228}$Th used in the present invention can be a physical mixture in which a $^{228}$Th salt has been ground into extremely fine particles to destroy its macroscopic crystal structure, and the super fine particles of $^{228}$Th are dispersed within a porous matrix, such as, for example, similarly powdered graphite, that will not absorb the $^{220}$Rn gas. The mixture can be compacted so that the $^{228}$Th is encapsulated within the graphite and forms a graphite disc 40 as shown in FIG. 2. This embodiment gives the $^{228}$Th sufficient bulk for handling purposes while allowing for the even diffusion of radon gas while preventing the formation of thorium crystals. Other inert materials which allow free diffusion of the $^{220}$Rn gas therethrough and are not subject to important decomposition by radiation may be used to form such a porous matrix for the $^{228}$Th, including but not limited to alumina and inert ceramic.

An alternate embodiment for the reactor of the present invention is shown in FIG. 2. The reactor 100 essentially comprises cylindrical body 110 whose cross section is in the form of a cross which is wider at the upper portion thereof. The body is externally threaded on the upper and lower portions. The gas permeable membrane 14 rests against the lip formed where the cylindrical chamber in body 110 increases in diameter, thereby separating the cylindrical chamber into a parental chamber 10 and a receiving chamber 12. To obtain the desired spacing for parental chamber 10, a seal ring 120 of appropriate thickness may be placed on top of diffusion membrane 14. A seal 130 is then slidably inserted into the upper portion of the body, where it is held in place against seal ring 120 by seal cap 140 which is threaded onto the upper portion of the body. An elongated plunger 150 is slidably inserted into the aperture in the bottom portion of the plunger body 110 so as to provide collection chamber 12 between the diffusion membrane 14 and the inner end of plunger 150. Plunger 150 is held in place by plunger cap 160 which is threaded onto the lower portion of plunger body 110. As before, all of the structural components of reactor 100 are preferably made from 316 stainless steel. However, since seal ring 120 must be compressible in addition to having a high melting point, it is preferred that it be made from materials such as gold, copper or nickel.

While the above described process is specific to the use of the generator as illustrated, and describes the best mode known for the practice of the invention, it should be apparent that other procedures could be utilized and other reactor embodiments fashioned to produce the lead isotope, relying on the same or comparable principles to effect the objects of this invention. For example, while the above described reactor utilizes a diffusion membrane to separate the two adjacent chambers, it is apparent that the reactor could be designed such that the two chambers are physically separated from each other and connected by a passageway through which the gaseous product could diffuse without permitting transfer of any solid material, e.g., a stopcock. Thus, when the stopcock is opened, the gaseous $^{220}$Rn diffuses from parental chamber 10 into the collection chamber 12. It is apparent that other such modifications could be made to the process and reactor without departing from the spirit of the invention.

Although the invention has been described with reference to the presently preferred embodiment, it should be understood that various modifications can be made without departing from the spirit of the invention. Accordingly, the invention is limited only by the following claims.

What is claimed is:

1. A method for obtaining daughter isotopes produced from parent isotopes by a chain of spontaneous decay which includes a normally gaseous intermediary isotope, comprising the steps of:

(a) providing said parent isotope in gas phase contact with a gas permeable barrier impervious to said parent isotope;

(b) permitting said gaseous intermediary isotope to diffuse through said gas permeable barrier into a chamber containing an open porosity porous medium;

(c) maintaining said gaseous intermediate in said medium for a time sufficient for at least a portion of said gaseous intermediate to decay to said daughter isotopes are captured by said open porosity porous medium; and (d) recovering said daughter isotopes from said receiving chamber.

2. The method of claim 1, wherein said parent isotope is maintained in a first closed chamber.

3. The method of claim 1, wherein said recovery step comprises dispersing said medium in water.

4. The method of claim 1, wherein said recovery step comprises dissolving said medium in water.

5. The method of claim 1, wherein said open porosity porous medium is urea.

6. The method of claim 1, wherein said open porosity porous medium is glucose.

7. The method of claim 1, wherein said open porosity porous medium is an inorganic salt.

8. The method of claim wherein said open porosity porous medium is lyophilized antibody.

9. The method of claim 1, wherein said lyophilized antibody is conjugated to a chelating agent.

10. The method of claim 1, wherein said open porosity porous medium is lyophilized microspheres.

11. The method of claim 1, wherein said immobilized parent isotope is in the form of a long hydrocarbon carboxylic acid salt.

12. The method of claim 11, wherein the long hydrocarbon carboxylic acid salt is prepared by a metathetical reaction from a second salt of said long hydrocarbon carboxylic acid which is freely soluble in water at room temperature.

13. The method of claim 12, wherein said second salt is selected from the group consisting of tetramethyl, tetraethyl, tetrabutyl and tetraisopropyl compounds.

14. A method for obtaining $^{212}$Pb, comprising the steps of:
  (a) providing $^{228}$Th in gas phase contact with a gas permeable barrier impervious to $^{228}$Th;
  (b) permitting gaseous $^{220}$Rn formed by the decay of $^{228}$Th to diffuse through the gas permeable barrier into a receiving chamber containing an open porosity porous medium;
  (c) maintaining said gaseous $^{220}$Rn in said receiving chamber for a time sufficient to permit at least a portion of the $^{220}$Rn to decay to $^{212}$Pb a portion of which $^{212}$Pb recoils into and is captured by the open porosity porous medium; and
  (d) recovering the $^{212}$Pb from said receiving chamber.

15. The method of claim 14, wherein said parent isotope is in the form of a long hydrocarbon carboxylic acid salt.

16. The method of claim 14, wherein said long hydrocarbon carboxylic acid is selected from the group consisting of stearic acid, palmitic acid, sebacic acid, caproic acid, lauric acid and myristic acid.

17. The method of claim 14, wherein said immobilized parent isotope is dispersed in a matrix of super fine particles comprising charcoal, graphite inert ceramics and alumina.

18. The method of claim 14, wherein said permeable barrier is a membrane.

19. The method of claim 14, wherein said open porosity porous medium is urea.

20. The method of claim 14, wherein said open porosity porous medium is glucose.

21. The method of claim 14, wherein said open porosity porous medium is a chloride.

22. The method of claim 14, wherein said open porosity porous medium is lyophilized antibody.

23. The method of claim 14, wherein said lyophilized antibody is conjugated to a chelating agent.

24. A generator for preparing radioisotopes produced from the decay of a parent isotope via a rare gas intermediary comprising:
  a parental chamber for immobilizing the parent isotope as it decays to the gaseous intermediary;
  a receiving chamber adjacent said parental chamber containing an open porosity porous medium;
  a diffusion means separating said container and said closed chamber which permits said gaseous intermediary to diffuse from said container into said closed chamber and prevents said parent isotope from entering said closed chamber, wherein as said gaseous intermediary decays the resulting radioactive isotopes recoil into said open porosity porous medium.

* * * * *

UNITED STATES PATENT AND TRADEMARK OFFICE
CERTIFICATE OF CORRECTION

PATENT NO. : 5,038,046
DATED : August 6, 1991
INVENTOR(S) : Norman et al.

It is certified that error appears in the above-indentified patent and that said Letters Patent is hereby corrected as shown below:

Column 3, line 24 delete "$3.3 \times 10^{12}$" and insert therefor-- "$3.3 \times {}^{-}10^{12}$--.

Column 6, line 61 delete "Supra" and insert therefor--<u>Supra</u>--.

Column 6, line 65 delete "a usual" and insert therefor -- an usual--.

Column 6, line 66 delete "$^{228}Rn$" and insert therefor --$^{220}Rn$--.

Signed and Sealed this

Twenty-ninth Day of November, 1994

Attest:

BRUCE LEHMAN

Attesting Officer    Commissioner of Patents and Trademarks